(12) United States Patent
Loccufier

(10) Patent No.: US 9,982,072 B2
(45) Date of Patent: May 29, 2018

(54) SYNTHESIS OF ACETAL COMPOUNDS

(71) Applicant: AGFA GRAPHICS NV, Mortsel (BE)

(72) Inventor: Johan Loccufier, Mortsel (BE)

(73) Assignee: AGFA NV, Mortsel (BE)

( * ) Notice: Subject to any disclaimer, the term of this patent is extended or adjusted under 35 U.S.C. 154(b) by 78 days.

(21) Appl. No.: 14/917,587

(22) PCT Filed: Oct. 22, 2014

(86) PCT No.: PCT/EP2014/072643
§ 371 (c)(1),
(2) Date: Mar. 9, 2016

(87) PCT Pub. No.: WO2015/062935
PCT Pub. Date: May 7, 2015

(65) Prior Publication Data
US 2016/0237185 A1  Aug. 18, 2016

(30) Foreign Application Priority Data
Oct. 30, 2013 (EP) ..................... 13190842

(51) Int. Cl.
| | | |
|---|---|---|
| *C08F 120/68* | (2006.01) | |
| *C07C 67/29* | (2006.01) | |
| *C07D 335/16* | (2006.01) | |
| *C09D 11/101* | (2014.01) | |
| *G03F 7/027* | (2006.01) | |
| *G03F 7/031* | (2006.01) | |
| *B01J 31/00* | (2006.01) | |
| *C07C 227/16* | (2006.01) | |
| *C09D 11/30* | (2014.01) | |
| *G03F 7/029* | (2006.01) | |
| *G03F 7/038* | (2006.01) | |

(52) U.S. Cl.
CPC ............. *C08F 120/68* (2013.01); *B01J 31/00* (2013.01); *C07C 67/29* (2013.01); *C07C 227/16* (2013.01); *C07D 335/16* (2013.01); *C09D 11/101* (2013.01); *C09D 11/30* (2013.01); *G03F 7/027* (2013.01); *G03F 7/029* (2013.01); *G03F 7/0295* (2013.01); *G03F 7/031* (2013.01); *G03F 7/038* (2013.01)

(58) Field of Classification Search
CPC ........ G03F 7/038; G03F 7/0295; G03F 7/029; G03F 7/037; B01J 31/00; C07C 227/16; C07D 7/031
See application file for complete search history.

(56) References Cited

U.S. PATENT DOCUMENTS

| | | | |
|---|---|---|---|
| 2005/0171062 A1 | 8/2005 | Old et al. | |
| 2011/0224324 A1* | 9/2011 | Loccufier | ............... C07C 69/54 522/34 |

FOREIGN PATENT DOCUMENTS

| | | | |
|---|---|---|---|
| EP | 2 199 273 | A1 | 6/2010 |
| WO | 2007/010483 | A1 | 1/2007 |
| WO | 2009/053305 | A1 | 4/2009 |
| WO | 2010/069758 | A1 | 6/2010 |
| WO | 2012/168458 | A1 | 12/2012 |

OTHER PUBLICATIONS

Official Communication issued in International Patent Application No. PCT/EP2014/072643, dated Dec. 9, 2014.

* cited by examiner

*Primary Examiner* — Sanza Mcclendon
(74) *Attorney, Agent, or Firm* — Keating and Bennett, LLP

(57) ABSTRACT

A process for the preparation of optionally asymmetric acetal compounds includes reacting a compound containing a hydroxyl group with a vinylether compound in the presence of a zwitterionic catalyst including at least one basic nitrogen containing structural fragment and at least one sulfonic acid group in its structure, with the proviso that a molar ratio of the basic nitrogen to sulfonic acid is 1:1.

15 Claims, 1 Drawing Sheet

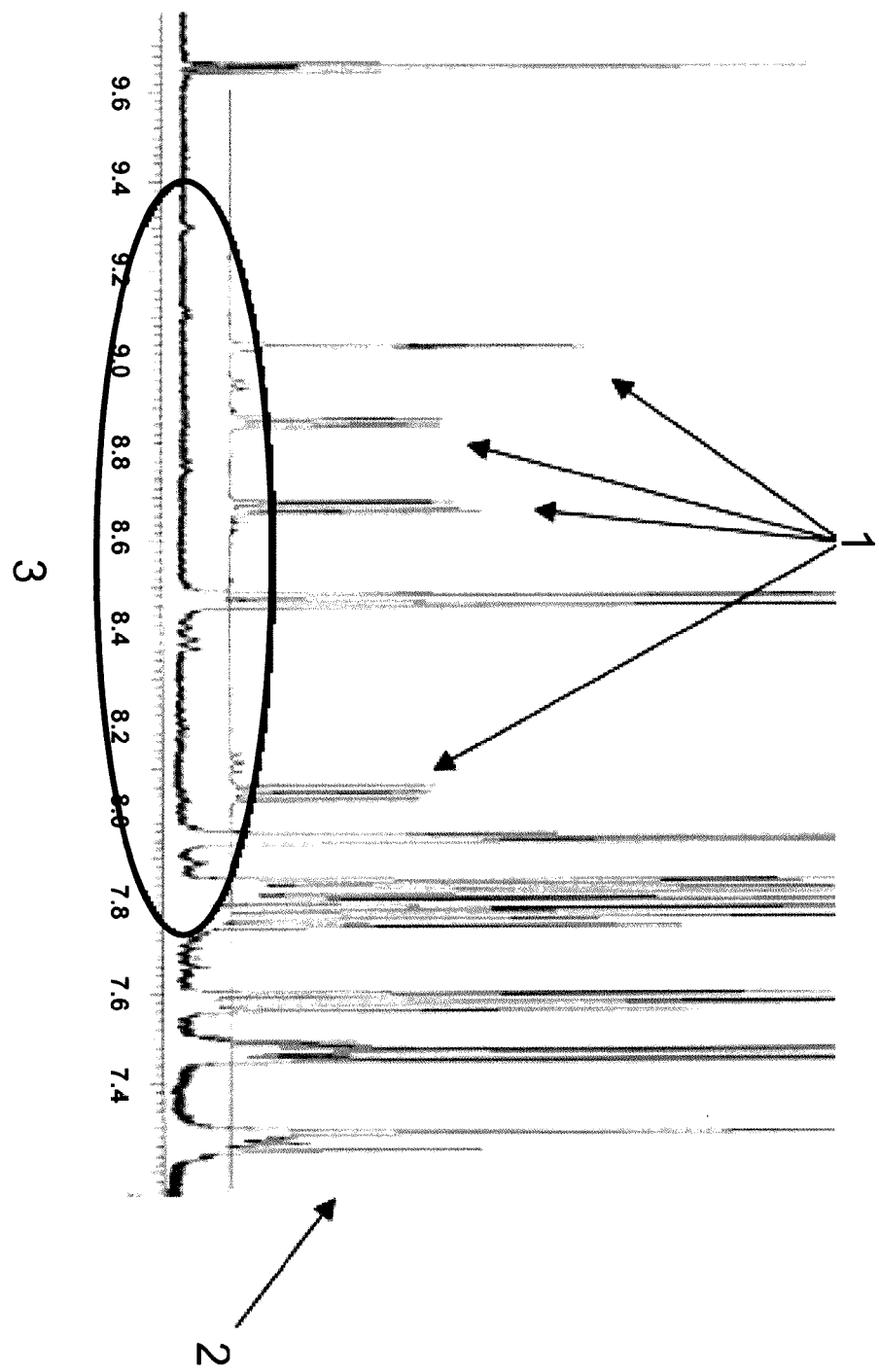

SYNTHESIS OF ACETAL COMPOUNDS

CROSS-REFERENCE TO RELATED APPLICATIONS

This application is a 371 National Stage Application of PCT/EP2014/072643, filed Oct. 22, 2014. This application claims the benefit of European Application No. 13190842.8, filed Oct. 30, 2013, which is incorporated by reference herein in its entirety.

BACKGROUND OF THE INVENTION

1. Field of the Invention

The present invention relates to the preparation of optionally asymmetric acetals from vinyl ethers and alcohols, using easily removable catalysts. More specifically, the present invention relates to the synthesis of polymerizable photoreactive compounds in reaction mixtures comprising high concentrations of vinyl ethers.

2. Description of the Related Art

Radiation curable compositions for food packaging require the use of low migrating photoreactive compounds. In digital printing techniques, such as ink jet, polymerizable photoreactive compounds are preferred for reasons of low viscosity. For both ecological and economical reasons, this requires an efficient synthesis of these polymerizable photoreactive compounds, wherein the solvent use, the number of steps and the number of isolations of both intermediates and end products in synthetic processes are minimized.

WO 2009/053305 (AGFA) discloses vinyl ether (meth)acylates, such as 2-(vinylethoxy)ethyl acrylate, as preferred monomers for the design of low migration ink jet inks.

The presence of the vinyl ether opens up the possibility to use the monomer of the ink carrier directly as reagent for the synthesis of polymerizable photoreactive compounds, without the need for isolating the polymerizable photoreactive compounds, as disclosed in WO 2010/069758 (AGFA).

This approach requires a highly efficient catalyst for the synthesis of asymmetric acetals from alcohol functionalized photoreactive compounds and vinyl ether containing monomers in the presence of high concentrations of these monomers. However, synthesis at elevated temperatures in highly concentrated vinylether monomer solutions can lead to spontaneous unwanted polymerization of the monomers, imposing considerable safety risks due to high exothermic polymerization leading to a thermal runaway.

For reasons of shelf life stability, the catalyst has to be removed from the end product to avoid degradation and side reactions upon storage. Furthermore for food packaging applications, the residual catalyst has also to be removed for migration reasons.

Typical catalysts used for the preparation of asymmetric acetals by addition of an alcohol to alkenyl-ethers, such as vinyl ethers, are protic acids with a sufficient low $pK_a$, such as hydrochloric acid, phosphoric acid, sulfonic acids, sulfuric acid, and carboxylic acids substituted with electron withdrawing groups such as fluorine and chlorine. Other preferred type of catalysts are organic salts of sulfonic acids, such as pyridine salts.

The use of hydrochloric acid has been disclosed in several documents (e.g. Trofimov et al., Tetrahedron Letters, 49, 3104-3107 (2008)).

The use of phosphoric acid has been disclosed by Toshiaki et al. (Tetrahedron Letters, 47, 3251-3255 (2006)).

The use of sulfonic acids as catalyst has been disclosed in numerous documents (e.g. Munro et al., Bioorganic and Medicinal chemistry, 16(3), 1279-1286 (2008); Snowden et al. Helvetica Chimica Acta, 89(12), 3071-3086 (2006), Lucatelli et al., Journal of Organic Chemistry, 67(26), 9468-9470 (2002); Wipf et al., Tetrahedron Letters, 40(28), 5139-5142 (1999)) Typical examples are p.-toluene sulfonic acid, 10-camphor sulfonic acid and methane sulfonic acid.

The use of sulfuric acid has been described by Rappe et al. (Justus Liebigs Annalen der Chemie, 601, 84-111 (1956)).

The use of carboxylic acids substituted with electron withdrawing substituents has been disclosed in a number of documents (e.g. Rivillo et al., Angewandte Chemie, International Edition, 46(38), 7247-72450 (2007); WO 2007/010483 (FIRMENICH); Alvarez de Cienfuego et al., Tetrahedron: asymmetry, 17(2), 1863-1866 (2006); US 2005171062 (ALLERGAN INC). Typical examples are trifluoroacetic acid and trichloroacetic acid.

The use organic salts of sulfonic acids has been disclosed in several documents (Lee et al. Bulletin of the Korean Chemical Society, 28(4), 513-514 (2007); Hattori et al., Organic Letters, 10(5), 717-720 (2008); Nakamura et al., Organic Letters, 10(2), 309-312 (2008); Nicolau et al. Journal of the American chemical Society, 129(48), 14850-14851 (2007); Nakamura et al., Tetrahedron, 63(35), 8670-8676 (2007)). A typical example of an organic salt of a sulfonic acid is pyridinium tosylate.

Occasionally, also Lewis acids have been reported as catalyst (Alper. H., Synthesis 1972, 81).

Several transition metals have also been shown effective as catalyst for the synthesis of asymmetric acetyls from alkenylethers and alcohols (Maity, G; Synth Commun 1993, 23, 1667; Iqbal, J; Synth Commun 1989, 19, 901; Kantam, M; Synth Commun 1993, 23, 2225; Bhuma, V; Synth Commun 1992, 22, 2941; Ma, S; Tetrahedron Lett 1993, 34, 5269; Molnar, A; Tetrahedron Lett 1996, 37, 8597).

Heterogeneous catalysis has been reported frequently (Bongini, A; Synthesis 1979, 618; Johnston, R; Synthesis 1988, 393; Olah, G; Synthesis 1983, 892; Menger, F; J Org Chem 1981, 46, 5044; Hoyer, S; Synthesis 1986, 655; Upadhya, T; Synth Commun 1996, 26, 4539; Campelo, J; Synth Commun 1994, 24, 1345; Bandgar, B; Synth Commun 1995, 25, 2211; Kumar, P; Synthesis 1993, 1069; Chavez, F; Synth Commun 1992, 22, 159; Patney, H; Synth Commun 1991, 21, 2329; Campelo, J; Synth Commun 1992, 22, 2335).

Acetonyl triphenylphoshonium derivatives have also been reported as catalysts for converting alcohols into asymmetric acetals (Hon et al., Tetrahedron, 57, 5991-6001).

In highly concentrated vinyl ether solutions, the use of strong acid catalysts, such as sulfonic acids, lead to cationic polymerizations as side reaction. This not only results in loss of yield of the desired compound but also leads to safety risks due to potential thermal runaways. Therefore, medium acidic catalysts, such as trifluoroacetic acid and pyridinium salts of sulfonic acids, are particularly preferred catalysts for use in highly concentrated vinyl ether solutions.

From a synthetic point of view, both soluble and resin based type of catalyst can be used. Soluble catalysts such as trifluoroacetic acid and trichloroacetic acid are often compatible with a broad scope of reaction circumstances. However, removal of the catalyst can be laborious, generating extra chemical waste and cost.

Resin based catalysts, such as crosslinked polyvinyl pyridinium sulfonates, are often easily removable from reaction mixtures by simple filtration. However, balancing the equivalence of sulfonic acid and pyridine moieties is not always straightforward in a solid crosslinked resin based catalyst. Small amounts of residual sulfonic acids can leach into the reaction mixture, acting as strong acid initiator for unwanted cationic polymerization.

Zwitterionic compounds are hardly being documented in the synthetic literature as catalysts for organic transformations, apart from WO 2012/168458 (ECOSYNTH BVBA), which discloses the use of a broad scope of zwitterionic catalysts in esterification reactions, using classic reaction conditions in solvent medium such as azeotropic removal of water.

Therefore, for both safety reasons and process simplicity there is still a need for a catalyst being intrinsically safe by avoiding potential excess of strong acids, while still being easily removable to avoid high process costs and waste generation.

SUMMARY OF THE INVENTION

It was found that the above problems for the synthesis of optionally asymmetric acetals in the presence of high concentrations of vinyl ethers, could be solved by using low molecular zwitterionic catalysts comprising at least one basic nitrogen containing structural fragment and at least one sulfonic acid in its structure, with the proviso that the molar ratio of the basic nitrogen to sulfonic acid is 1:1.

These zwitterionic catalysts were found to be easily removable. Excess of strong acid was avoided by the nature of the catalyst. Especially zwitterionic catalysts wherein the at least one basic nitrogen containing structural fragment was selected from the group consisting of a substituted or unsubstituted pyridine, quinoline, isoquinoline, imidazole, benzimidazole and an aniline group, were found to be very effective.

It is an object of the present invention to provide a synthetic method for optionally asymmetric acetals as defined below.

It is a further object of the present invention to provide a synthetic process for the synthesis of optionally asymmetric acetals in the presence of high concentrations of vinyl ethers. High concentrations of vinyl ethers meaning that the reaction medium can consist essentially of vinyl ether compounds, or that the reaction medium contains the vinylether compound in a molar ratio over the catalyst of at least 50, preferably at least 100. A molar ratio of 100 or more is preferred for reasons of productivity, since a higher amount of photoreactive compounds containing a hydroxyl group can be dissolved.

It is a further object of the present invention to provide a synthetic process for the synthesis in the presence of high concentrations of vinyl ethers of optionally asymmetric acetals which further contain at least one other free radical polymerizable ethylenically unsaturated group.

It is a further objective of the present invention to provide a synthetic approach for the synthesis of polymerizable photoreactive compounds in the presence of high concentrations of vinyl ethers further comprising at least one other free radical polymerizable ethylenically unsaturated group.

It is a further objective of the present invention to provide a synthetic approach for the synthesis of polymerizable photoreactive compounds, suitable for radiation curable formulations for food packaging applications.

These and other objectives of the present invention will become apparent in the detailed description hereinafter.

BRIEF DESCRIPTION OF THE DRAWINGS

FIG. 1 discloses the spectrum 2 obtained by $^1$H-NMR analysis in Example 1, wherein no 3-pyridine sulfonic acid peaks 1 are visible in the region 3 of the spectrum 2 of the VEEA solution of the acrylated photoinitiator.

DETAILED DESCRIPTION OF THE PREFERRED EMBODIMENTS

Definitions

The term "alkyl" means all variants possible for each number of carbon atoms in the alkyl group i.e. methyl, ethyl, for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethyl-propyl and 2-methyl-butyl, etc.

Unless otherwise specified a substituted or unsubstituted alkyl group is preferably a $C_1$ to $C_6$-alkyl group.

Unless otherwise specified a substituted or unsubstituted alkenyl group is preferably a $C_1$ to $C_6$-alkenyl group.

Unless otherwise specified a substituted or unsubstituted alkynyl group is preferably a $C_1$ to $C_6$-alkynyl group.

Unless otherwise specified a substituted or unsubstituted aralkyl group is preferably a phenyl or naphthyl group including one, two, three or more $C_1$ to $C_6$-alkyl groups.

Unless otherwise specified a substituted or unsubstituted alkaryl group is preferably a $C_7$ to $C_{20}$-alkyl group including a phenyl group or naphthyl group.

Unless otherwise specified a substituted or unsubstituted aryl group is preferably a phenyl group or naphthyl group Unless otherwise specified a substituted or unsubstituted heteroaryl group is preferably a five- or six-membered ring substituted by one, two or three oxygen atoms, nitrogen atoms, sulphur atoms, selenium atoms or combinations thereof.

The term "substituted", in e.g. substituted alkyl group means that the alkyl group may be substituted by other atoms than the atoms normally present in such a group, i.e. carbon and hydrogen. For example, a substituted alkyl group may include a halogen atom or a thiol group. An unsubstituted alkyl group contains only carbon and hydrogen atoms Unless otherwise specified a substituted alkyl group, a substituted alkenyl group, a substituted alkynyl group, a substituted aralkyl group, a substituted alkaryl group, a substituted aryl and a substituted heteroaryl group are preferably substituted by one or more constituents selected from the group consisting of methyl, ethyl, n-propyl, isopropyl, n-butyl, isobutyl and tertiary-butyl, ester group, amide group, ether group, thioether group, ketone group, aldehyde group, sulfoxide group, sulfone group, sulfonate ester group, sulphonamide group, —Cl, —Br, —I, —OH, —SH, —CN and —NO$_2$.

The term "image" includes text, numbers, graphics, logos, photos, barcodes, QR codes, and the like. An image can be defined in 1 or more colours.

Process

A process for the preparation of optionally asymmetric acetal compounds, according to a preferred embodiment of the present invention comprises reacting a compound containing a hydroxyl group with a vinylether compound in the presence of a zwitterionic catalyst including at least one basic nitrogen containing structural fragment and at least one sulfonic acid group in its structure, with the proviso that the molar ratio of the basic nitrogen to sulfonic acid is 1:1.

In a preferred embodiment of the process according to the invention, the at least one basic nitrogen containing structural fragment is selected from the group consisting of a pyridine group, a quinoline group, an isoquinoline group, an imidazole group, a benzimidazole group and an aniline group.

In a more preferred embodiment of the process according to the invention, the at least one basic nitrogen containing structural fragment is selected from the group consisting of an unsubstituted pyridine group, an unsubstituted quinoline group, an unsubstituted isoquinoline group, an unsubstituted imidazole group, an unsubstituted benzimidazole group and an unsubstituted aniline group.

In a preferred embodiment of the process according to the invention, the vinylether compound includes at least one vinylether group and at least one other free radical polymerizable ethylenically unsaturated group selected from the group consisting of an acrylate group, a methacrylate group, an acrylamide group, a methacrylamide group, a styrene group, a maleimide group, a vinyl ester group, a vinyl ether group, an allyl ether group and an allyl ester group.

In a more preferred embodiment of the process according to the invention, the at least one other polymerizable ethylenically unsaturated group is an acrylate group.

In a preferred embodiment of the process according to the invention, the compound containing a hydroxyl group is a photoreactive compound containing a hydroxyl group, more preferably the photoreactive compound containing a hydroxyl group is a photoinitator or a co-initiator containing a hydroxyl group.

In a preferred embodiment of the process, the zwitterionic catalyst is used in a concentration of 0.5 to 20 mol % of the compound containing a hydroxyl group, more preferably 1 to 15 mol % of the compound containing a hydroxyl group and most preferably 3 to 10 mol % of the compound containing a hydroxyl group.

The zwitterionic catalyst is compatible with batch, semi batch and continuous synthetic processes.

Although the zwitterionic catalyst can be applied to any synthesis of both symmetric and asymmetric acetals, the catalyst is particularly useful in synthetic processes in highly reactive environment, containing a high concentration of vinyl ethers.

In a process according to a preferred embodiment of the present invention, the starting reaction mixture preferably contains at least 25 wt % by weight of the vinyl ether compound, more preferably at least 35 wt % and most preferably at least 45 wt %, with all wt % being based on the total weight of the reaction mixture.

The process according to a preferred embodiment of the present invention is particularly useful for the preparation of polymerizable photoreactive compounds for food packaging applications.

A particularly preferred synthetic process according to the present invention can be represented by general scheme:

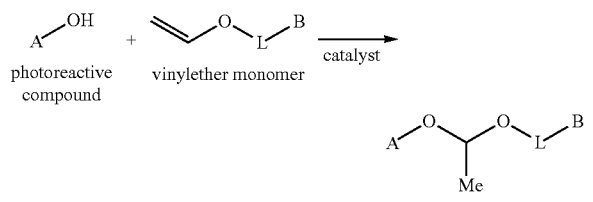

wherein, A represent a structural moiety comprising a photoreactive group; L represents a divalent linking group selected from the group consisting of a substituted or unsubstituted alkylene group, alkenylene group, alkynylene group, arylene group and a substituted or unsubstituted aliphatic ether containing group; B represents a free radical polymerizable group selected from the group consisting of an acrylate, a methacrylate, an acrylamide, a methacryl amide, a fumarate, a maleate and an itaconate; with the proviso that the starting reaction mixture comprises at least 25 wt % of vinylether monomer based on the total weight of the starting reaction mixture.

Optionally, aprotic organic cosolvents can be used in the synthetic process. Preferred classes of cosolvents are selected from the group consisting of esters, such as ethyl acetate, isopropyl acetate, butyl acetate and the like, ketones, such as acetone, methyl ethyl ketone, methyl isobutyl ketone and the like and ethers, such as methyl tertiary butyl ether. Preferably, the amount of cosolvent is less then 40 wt % of starting reaction mixture. More preferably no aprotic organic cosolvents are used.

Zwitterionic Catalysts

The zwitterionic catalyst used in the process according to a preferred embodiment of the present invention comprises at least one basic nitrogen containing structural fragment and at least one sulfonic acid in its structure, with the proviso that the molar ratio of the basic nitrogen to sulfonic acid is 1:1.

The zwitterionic catalyst is preferably selected from the group consisting of sulfonated pyridines, quinolines, isoquinolines, imidazoles, benzimidazoles and anilines.

In a preferred embodiment, the zwitterionic catalyst according to the present invention is represented by Formula (I):

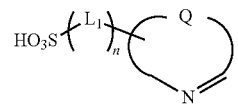

Formula (I), wherein, $L_1$ represents a divalent linking group selected from the group consisting of a substituted or unsubstituted alkylene group, alkenylene group, alkynylene group and arylene group; n represents 0 or 1; and Q represents the necessary atoms to form a substituted or unsubstituted pyridine ring. The divalent linking group $L_1$ preferably contains 1 to 20 carbon atoms.

In a preferred embodiment, the catalyst according to the present invention is selected from the group consisting of 2-pyridine sulfonic acid, 3-pyridine sulfonic acid and 4-pyridine sulfonic acid.

Preferred catalysts used in the process according to the present invention are shown in Table 1, without being limited thereto.

TABLE 1

| | |
|---|---|
| (3-pyridinesulfonic acid structure) | cat-1 |
| (2-pyridinesulfonic acid structure) | cat-2 |
| (4-pyridinesulfonic acid structure) | cat-3 |

TABLE 1-continued

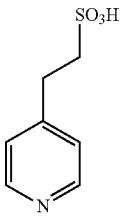 cat-4

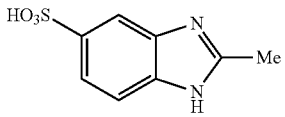 [SMILES: Cc1nc2cc(S(=O)(=O)O)ccc2[nH]1] cat-5

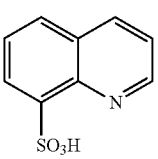 cat-6

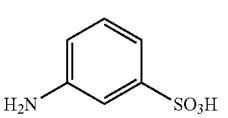 cat-7

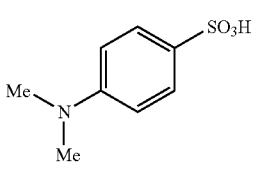 [SMILES: CN(C)c1ccc(S(=O)(=O)O)cc1] cat-8

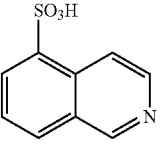 [SMILES: O=S(=O)(O)c1cccc2cnccc12] cat-9

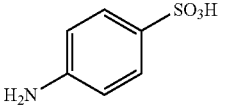 [SMILES: Nc1ccc(S(=O)(=O)O)cc1] cat-10

Vinylether Compounds

The vinylether compound includes at least one vinylether group. In addition to the at least one vinylether group, the vinylether compound preferably includes at least one other free radical polymerizable ethylenically unsaturated group selected from the group consisting of an acrylate group, a methacrylate group, an acrylamide group, a methacrylamide group, a styrene group, a maleimide group, a vinyl ester group, a vinyl ether group, an allyl ether group and an allyl ester group; more preferably includes at least one other free radical polymerizable ethylenically unsaturated group selected from the group consisting of an acrylate group, a methacrylate group, an acrylamide group, a methacrylamide group, a styrene group, a maleimide group, a vinyl ester group, an allyl ether group and an allyl ester group.

The vinylether compound includes preferably at least one vinylether group and at least one (meth)acrylate group, more preferably at least one vinylether group and at least one acrylate group.

In a preferred embodiment, the vinyl ether compound is represented by Formula (II):

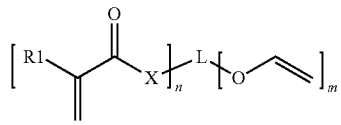

Formula (II), wherein, $R^1$ represents a hydrogen or a substituted or unsubstituted alkyl group; L represents a linking group; m and n independently represent a value from 1 to 5; X represents O, S or $NR^2$ with $R^2$ having the same meaning as $R^1$; with the proviso that if $X=NR^2$, that L and $R^2$ may form together a ring system. The ring of the system formed by L and $R^2$ consists preferably of 5 or 6 atoms.

In a more preferred embodiment, the vinyl ether compound is represented by Formula (III):

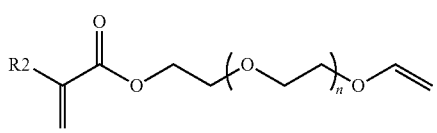

Formula (III), wherein, $R^2$ represents a hydrogen or a methyl group; and n represents an integer from 0 to 4. In an even more preferred embodiment, R represent a hydrogen. In the most preferred embodiment $R^2$ represents hydrogen and n is equal to 1. Preferred vinyl ether compounds are monomers given in Table 2 without being limited thereto.

TABLE 2

| | |
|---|---|
| 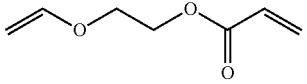 | Mono-1 |
| 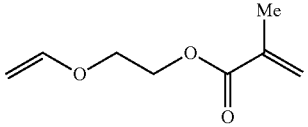 | Mono-2 |
| 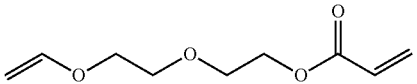 | Mono-3 |
| 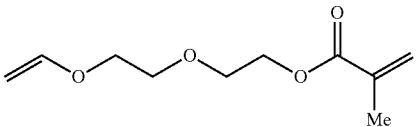 | Mono-4 |
| 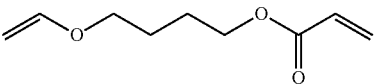 | Mono-5 |
| 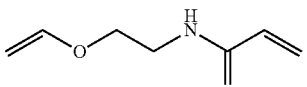 | Mono-6 |

TABLE 2-continued

| | |
|---|---|
| 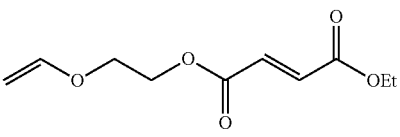 | Mono-7 |
| 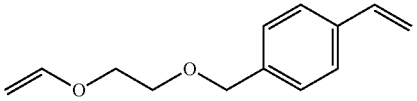 | Mono-8 |
| 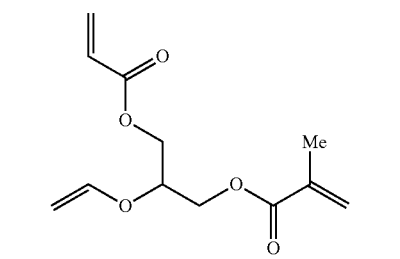 [SMILES: C=COC(COC(=O)C=C)COC(=O)C(=C)C] | Mono-9 |
| 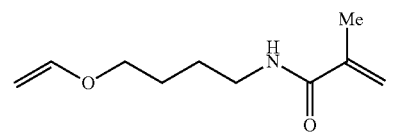 | Mono-10 |

Compounds Containing a Hydroxyl Group

The compound containing a hydroxyl group is preferably a photoreactive compound and can be represented by the formula A-OH, wherein A represents the photoreactive group. The photoreactive group A is defined as an organic moiety useful in radiation curable compositions as photoinitiator or coinitiator.

In a preferred embodiment, the photoreactive compound containing a hydroxyl group is selected from the group consisting of a Norrish type I photoinitiator, a Norrish type II photoinitiator and a tertiary amine coinitiator.

Preferred Norrish type I photoinitiators are selected from the group consisting of benzoinethers, benzil ketals, α,α-dialkoxyacetophenones, α-hydroxyalkylphenones, α-aminoalkylphenones, acylphosphine oxides, acylphosphine sulphides, α-haloketones, α-halosulfones and phenylglyoxalates.

Preferred Norrish type II photoinitiators are selected from the group consisting of benzophenones, thioxanthones, 1,2-diketones and anthraquinones.

Dialkyl anilines are preferred as coinitiator. More preferably the coinitiator is a dialkylamino benzoic acid derivative. Most preferably the coinitiator is a 4-dimethylamino benzoic acid derivative.

Particularly preferred hydroxyl functionalized photoreactive compounds A-OH are given in Table 3 without being limited thereto.

TABLE 3

| | |
|---|---|
| 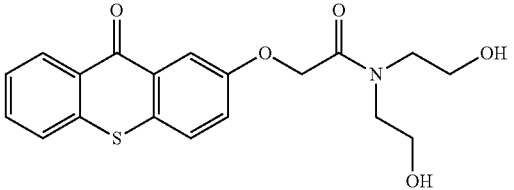 [SMILES: O=C(COc1ccc2sc3ccccc3c(=O)c2c1)N(CCO)CCO] | Photo-1 |
| 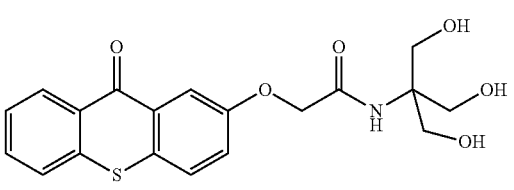 [SMILES: O=C(COc1ccc2sc3ccccc3c(=O)c2c1)NC(CO)(CO)CO] | Photo-2 |
| 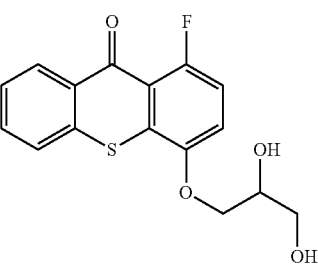 [SMILES: O=c1c2ccccc2sc2c(OCC(O)CO)ccc(F)c12] | Photo-3 |

TABLE 3-continued

| | |
|---|---|
| (structure) | Photo-4 |
| (structure) | Photo-5 |
| (structure) | Photo-6 |
| (structure) | Photo-7 |
| (structure) | Photo-8 |
| (structure) | Photo-9 |
| (structure) | Photo-10 |
| (structure) | Photo-11 |
| (structure) | Photo-12 |

TABLE 3-continued

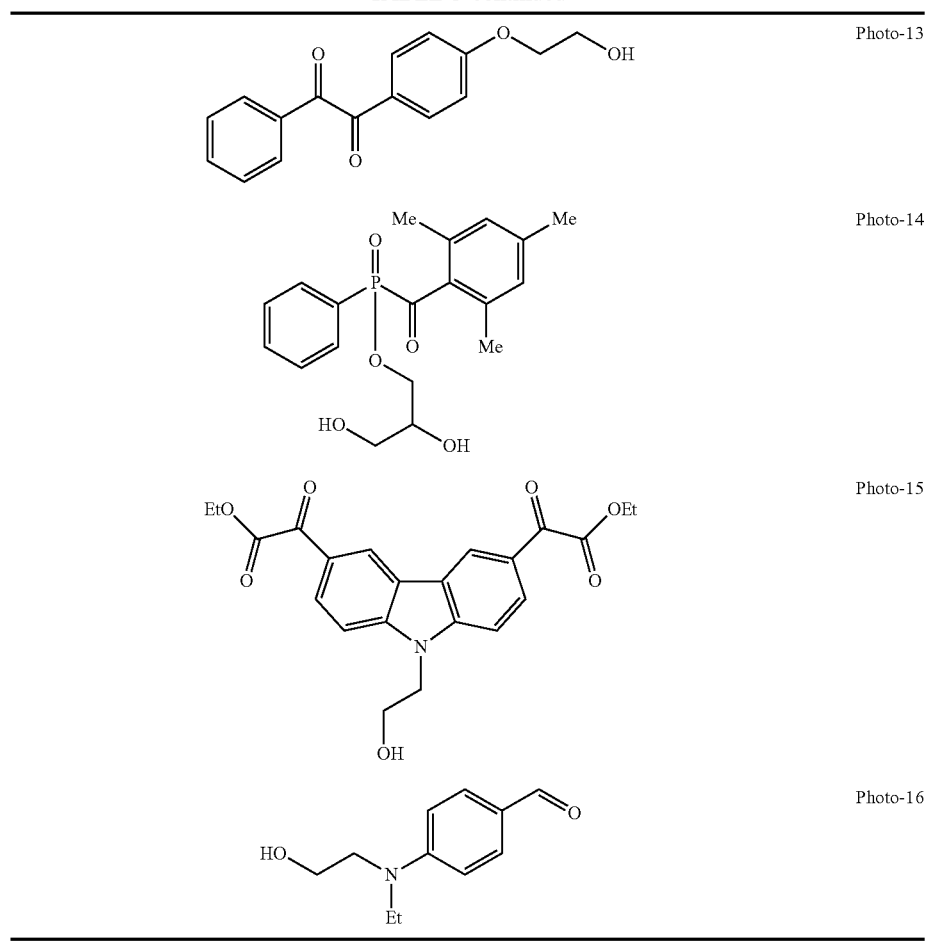

Photo-13

Photo-14

Photo-15

Photo-16

Photoreactive Compositions

A preferred result of the process according to the present invention is a polymerizable composition consisting essentially of:
a) a polymerizable photoreactive compound including at least one acetal;
b) a vinylether compound containing at least one other polymerizable group;
c) no more than 0.1 wt % of a zwitterionic catalyst comprising at least one basic nitrogen containing structural fragment and at least one sulfonic acid group in its structure, with the proviso that the molar ratio of the basic nitrogen to sulfonic acid is 1:1;
d) optionally one or more polymerization inhibitors; and
e) optionally one or more free radical polymerizable compounds differing from the vinylether compound containing at least one other polymerizable group; wherein the wt % is based on the total weight of the polymerizable composition.

Photoreactive compositions containing the zwitterionic catalyst but in a concentration of no more than 0.1 wt % exhibited excellent stability, which was not observed for photoreactive compositions containing trifluoroacetic acid or pyridinium tosylate as catalyst or resulting from a synthesis using sulfonic acid substituted ion exchangers or crosslinked poly(vinylpyridine) tosylate resin. Preferably, the photoreactive composition contains the zwitterionic catalyst in a concentration of no more than 0.05 wt % based on the total weight of the photoreactive composition.

Preferred free radical polymerizable compounds differing from the vinylether compound containing at least one other polymerizable group are monofunctional, difunctional and polyfunctional acrylates.

The optional one or more polymerization inhibitors and the optional one or more free radical polymerizable compounds differing from the vinylether compound containing at least one other polymerizable group taken together are preferably present in the photoreactive composition in amount of no more than 25 wt %, more preferably no more than 10 wt % of the photoreactive composition with the wt % based on the total weight of the photoreactive composition. Most preferably no free radical polymerizable compounds differing from the vinylether compound containing at least one other polymerizable group is present in the photoreactive composition.

Polymerization Inhibitors

The photoreactive composition may contain a polymerization inhibitor.

A preferred polymerization inhibitor is butylhydroxytoluene for reasons of food safety.

Suitable polymerization inhibitors include phenol type antioxidants, hindered amine light stabilizers, phosphor type antioxidants, hydroquinonemonomethyl ether commonly used in (meth)acrylate monomers, and hydroquinone, t-butylcatechol, pyrogallol may also be used.

Suitable commercial inhibitors are, for example, Sumilizer™ GA-80, Sumilizer™ GM and Sumilizer™ GS produced by Sumitomo Chemical Co. Ltd.; Genorad™16, Genorad™ 18 and Genorad™ 20 from Rahn AG; Irgastab™ UV10 and Irgastab™ UV22, Tinuvin™ 460 and CGS20 from BASF; Floorstab™ UV range (UV-1, UV-2, UV-5 and UV-8) from Kromachem Ltd, Additol™ S range (S100, S110, S120 and S130) from Cytec Surface Specialties.

Since excessive addition of these polymerization inhibitors will lower the ink sensitivity to curing, the amount of a polymerization inhibitor is preferably less than 1 wt % of the photoreactive composition.

Free Radical Polymerizable Compounds

The free radical polymerizable compounds differing from the vinylether compound are monomers and oligomers that are preferably purified compounds having no or almost no impurities, more particularly no toxic or carcinogenic impurities. The impurities are usually derivative compounds obtained during synthesis of the polymerizable compound. Purification methods are well-known to those skilled in the art of manufacturing monomers and oligomers.

Sometimes, however, some compounds may be added deliberately to pure polymerizable compounds in harmless amounts, for example, polymerization inhibitors or stabilizers.

Particularly preferred monomers and oligomers are those listed in [0106] to [0115] in EP 1911814 A (AGFA), especially those containing an acrylate group.

Industrial Applicability

The photoreactive compositions can be advantageously used in radiation curable inkjet inks and varnishes because of their low viscosity, especially in radiation curable inkjet inks and varnishes for printing of food or pharma packaging.

The preparation of radiation curable inkjet inks is well-known to the skilled person. Preferred methods of preparation are disclosed in paragraphs [0076] to [0085] of WO 2011/069943 (AGFA).

There is no real limitation on the type of substrate for printing. The substrates may have ceramic, metallic, paper or polymeric surfaces for printing. The substrate may be porous, as e.g. textile, paper and card board substrates, or substantially non-absorbing substrates such as e.g. a substrate having a polyethyleneterephthalate surface.

Preferred substrates include surfaces or consist of polyethylene, polypropylene, polycarbonate, polyvinyl chloride, polyesters like polyethylene terephthalate (PET), polyethylene naphthalate (PEN) and polylactide (PLA) and polyimide.

EXAMPLES

Materials

All compounds and solvents were readily available from fine chemical suppliers such as Acros or Aldrich unless otherwise specified. The water used was demineralized water.

VEEA is the difunctional monomer 2-(2-vinyloxyethoxy) ethyl acrylate available from Nippon Shokubai, Japan.

Omnipol™ TX is the di-ester of carboxymethoxy-thioxanthone and polytetramethyleneglycol 250, average MW of 790 and available from IGM Resins, Waalwijk, NL.

Esacure™ KIP160 is supplied by Lamberti and has the formula:

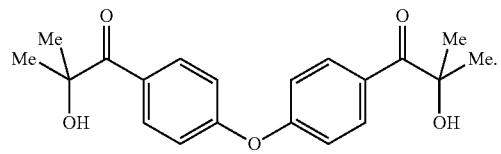 [SMILES: CC(C)(O)C(=O)c1ccc(Oc2ccc(C(=O)C(C)(C)O)cc2)cc1]

BHT is butylhydroxytoluene.

Example 1

This example describes the synthesis of a copolymerizable thioxanthone using 3-pyridine sulfonic acid as zwitterionic catalyst.

Synthesis

Reaction scheme:

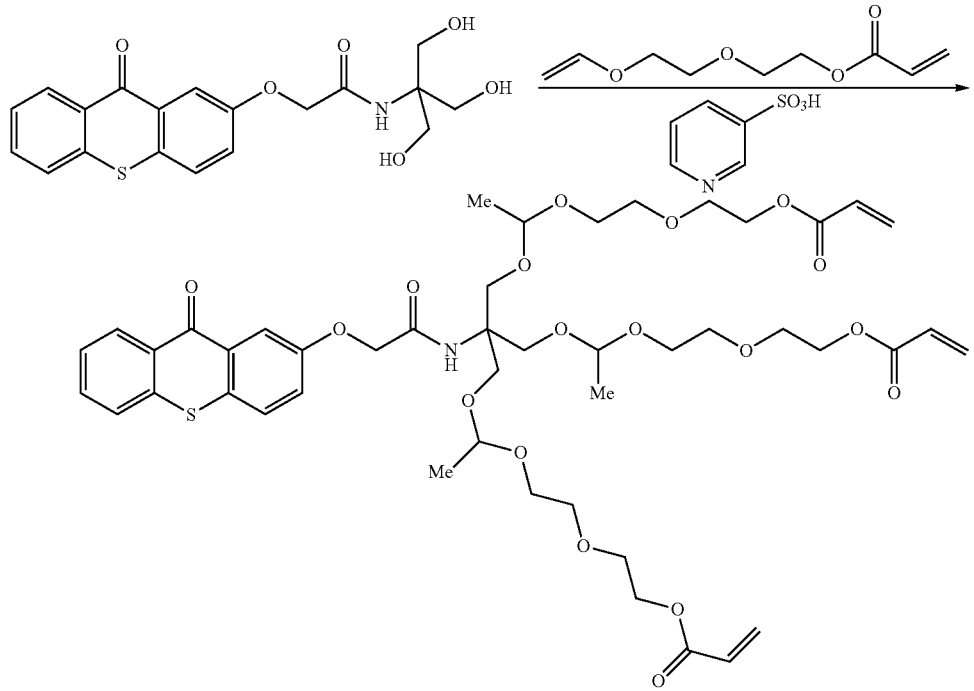

The starting thioxanthone Photo-2 was prepared according to the following procedure:

395 g Omnipol™ TX was dissolved in 1850 ml dimethyl sulfoxide. The reaction mixture was heated to 60° C. and 363 g (3 mol) tris(hydroxymethyl) amino methane and 415 g (3 mol) potassium carbonate were added. The reaction was allowed to continue for 2 hours at 60° C. The reaction mixture was allowed to cool down to room temperature. The precipitated salts were removed by filtration and the reaction mixture was added to a mixture of 1500 ml water and 250 ml acetone. The thioxanthone precipitated from the medium, was isolated by filtration and dried. The crude thioxanthone was treated with 1500 ml acetone, isolated by filtration and dried. 260 g of the thioxanthone Photo-2 was isolated (TLC-analysis: RP-C18 (Partisil KC18F, supplied by Whatman), eluent MeOH/0.5 M NaCl 85/15, $R_f$=0.71).

The catalytic addition of VEEA by 3-pyridine sulfonic acid:

17.12 g (44 mmol) of the intermediate thioxanthone was added to a mixture of 40.92 g (0.22 mol) 2-(2-vinyloxy-ethoxy)ethyl acrylate and 25.35 g isopropyl acetate. 700 mg (4.4 mmol) 3-pyridine sulfonic acid was added and the mixture was heated to 85° C. for 7 hours. TLC-analysis indicated complete conversion to the desired end product ((TLC on Partisil KC18F, supplied by Whatman, eluent MeOH/0.5 M NaCl 85/15, $R_f$: 0.3). The reaction mixture was allowed to cool down to room temperature and the catalyst was removed by filtration. The isopropyl acetate was removed under reduced pressure. Based on a detailed TLC analysis of the thioxanthone solution in 2-(2-vinyloxyethoxy)ethyl acrylate no residual catalyst was detectable (TLC analysis on Partisil KC18F, eluent MeOH/0.5 M NaCl 85/15; $R_f$ of the reference compound under the same analytical circumstances: 0.94)

The TLC analysis was confirmed by $^1$H-NMR analysis (50 μl of the above described VEEA solution in 650 μl DMSO-d6) as shown in FIG. 1 by the aromatic part of the spectrum.

This example illustrates the smooth conversion of alcohol functionalized photoreactive groups using an easily removable zwitterionic catalyst. The isolated thioxanthone solution can directly be implemented into radiation curable inks for food packaging, as no catalyst residues were detectable.

Example 2

This example illustrates the variability of photoreactive groups that can be transferred into asymmetric acetals using zwitterionic catalysts according to the present invention.

Synthesis

General reaction scheme:

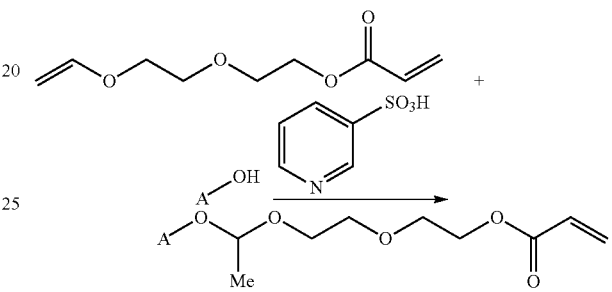

100 mg BHT was added to each reaction mixture.

The following photoreactive compounds, photoinitiators INI-1 to INI-3 and co-initiator COINI-1, were prepared according to the above general reaction scheme using the reaction conditions according to Table 4. The $R_f$ value was determined by TLC on Partisil KC18F using as eluent MeOH/0.5 M NaCl in ratio 85/15.

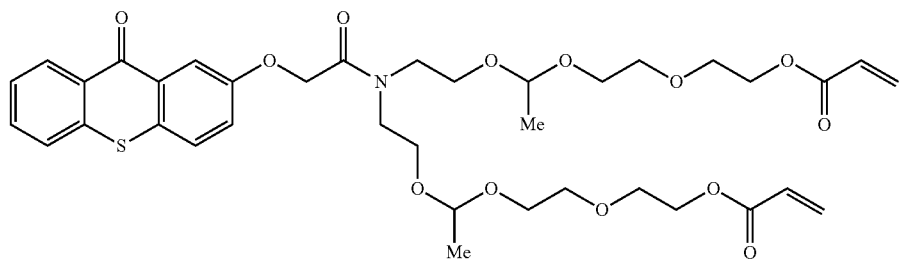

INI-1

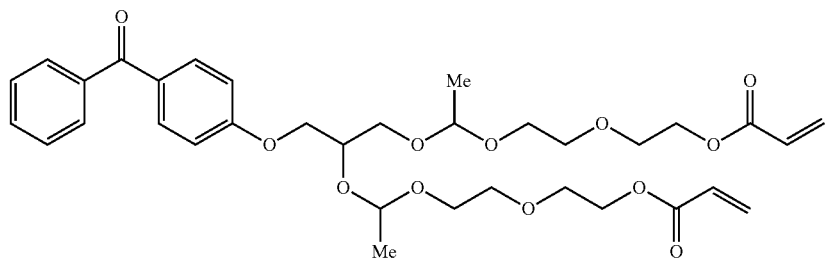

INI-2

COINI-1

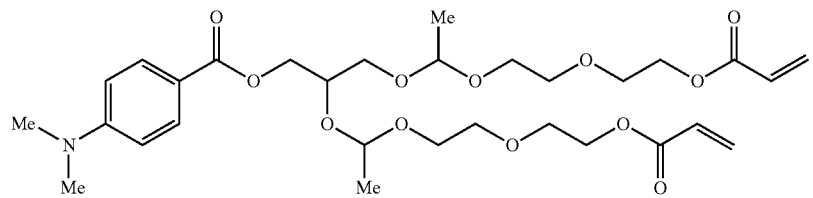

INI-3

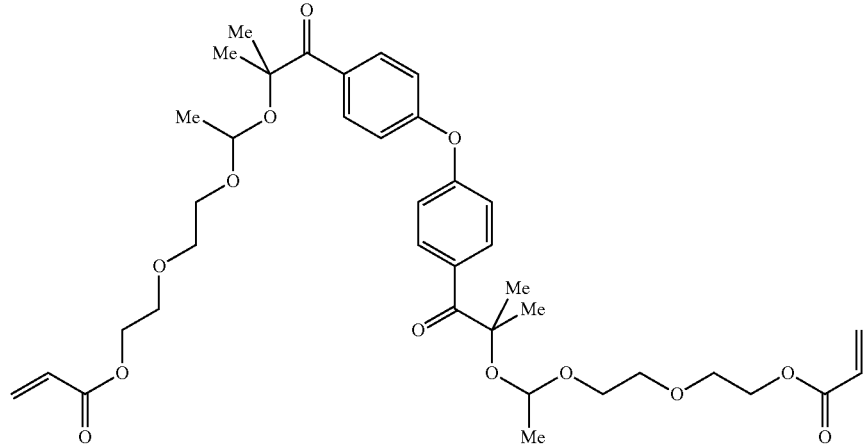

TABLE 4

| A-OH | | Reaction Product | VEEA g | 3-pyridine sulfonic acid g | Reaction Time (hours) | Reaction Temp. (° C.) | $R_f$ |
|---|---|---|---|---|---|---|---|
| Type | g | | | | | | |
| Photo-1 | 11.2 | INI-1 | 63.3 | 0.5 | 22 | 85 | 0.33 |
| Photo-5 | 5.4 | INI-2 | 37.2 | 0.3 | 22 | 75 | 0.37 |
| Photo-8 | 7.2 | COINI-1 | 54.0 | 0.5 | 22 | 75 | 0.47 |
| Photo-7 | 10.3 | INI-3 | 63.3 | 0.5 | 22 | 75 | 0.25 |

Photo-1 and Photo-5 were prepared according to WO 2010/069758 A (AGFA) in the same manner as for STIN-10, respectively STIN-18.

Photo-8 was prepared according to the following scheme:

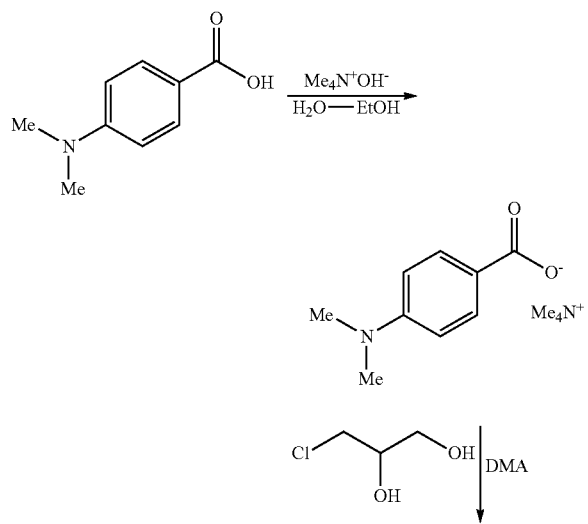

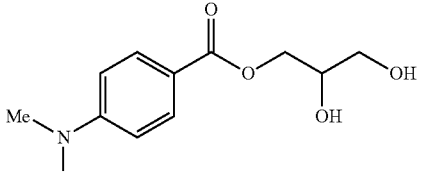

47.4 g of a 25 w % solution of tetramethyl ammonium hydroxide (0.13 mol) was added to a suspension of 21.5 g (0.13 mol) of 4-dimethylamino benzoic acid in a mixture of 500 ml ethanol en 130 ml water. The mixture was stirred for one hour and the solvent was evaporated under reduced pressure. 30 g of the isolated tetramethyl ammonium salt of 4-dimethylamino benzoic acid was dissolved in 250 ml dimethyl acetamide (DMA). 43.1 g (0.39 mol) of 3-chloro-1,2-propane diol was added and the reaction was allowed to continue for 24 hours at 82° C. The reaction mixture was allowed to cool down to room temperature and the solvent was evaporated under reduced pressure. The oily residue was dissolved in 300 ml ethyl acetate and extracted twice with 330 ml of a 1 N NaOH solution. The organic fraction was isolated, dried over $MgSO_4$ and evaporated under reduced pressure. 25.4 g of 4-dimethylamino-benzoic acid 2,3-dihydroxy-propyl ester was isolated (y: 81.7%, TLC on Partisil KC18F, eluent MeOH/0.5 M NaCl 70/30: $R_f$: 0.56)

The commercial photoinitiator Esacure™ KIP160 was used for Photo-7.

In all cases the catalyst was removed by filtration, without a detectable trace of residual catalyst (TLC analysis on Partisil KC18F, eluent MeOH/0.5 M NaCl 85/15; $R_f$ of the reference compound under the same analytical circumstances: 0.94)

Hence it should be clear from the above example that a wide variety of photoreactive compounds can be converted into polymerizable photoreactive compounds using the zwitterionic catalyst. It should also be clear that the catalyst can easily be removed from the reaction mixture, making the VEEA solution of the different photoreactive compounds directly useable in radiation curable inks for food packaging printing applications.

Example 3

This example illustrates the variability of zwitterionic catalysts that can be used in a synthetic process according to the present invention.

Synthesis

General reaction scheme:

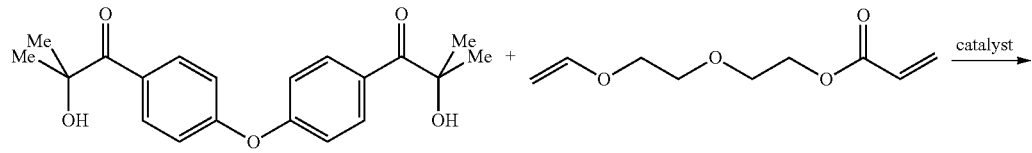

TABLE 5

| Catalyst | | Photo-7 | VEEA | Reaction Temp. | Time for full |
|---|---|---|---|---|---|
| Type | g (mmol) | g (mmol) | g (mol) | (° C.) | conversion |
| Cat-4 | 0.6 (3.2) | 10.3 (30.1) | 63.3 (0.34) | 75 | 24 h |
| Cat-6 | 0.6 (2.9) | 10.3 (30.1) | 63.3 (0.34) | 75 | 17 h |

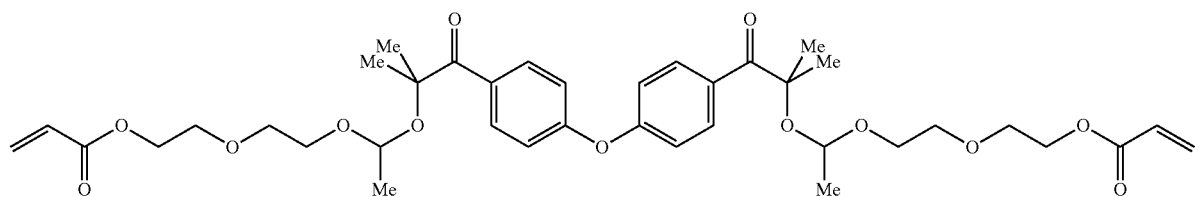

The photoreactive compound INI-3 was prepared from Photo-7 (Esacure™ KIP160) according to the above general reaction scheme using the reaction conditions according to Table 5. 0.1 g BHT was added to each reaction mixture to avoid unwanted free radical polymerization.

TABLE 5-continued

| | Catalyst | Photo-7 | VEEA | Reaction | |
|---|---|---|---|---|---|
| Type | g (mmol) | g (mmol) | g (mol) | Temp. (° C.) | Time for full conversion |
| Cat-2 | 0.5 (3.1) | 10.3 (30.1) | 63.3 (0.34) | 55 | 2 h |
| Cat-7 | 0.5 (2.9) | 10.3 (30.1) | 63.3 (0.34) | 75 | 23 h |

Upon complete conversion, the reaction mixtures were allowed to cool down to room temperature and the catalysts were easily removed by filtration. No residual catalyst could be detected in the VEEA solutions of INI-3.

The conversion was followed using Thin Layer Chromatography on Partisil KC18F, supplied by Whatman, using MeOH/0.5 M NaCl 85/15 as eluent. The $R_f$-values of the most important components are given in Table 8.

TABLE 8

| Structure | $R_f$ |
|---|---|
| Photo-7 | 0.61 |
| INI-3 | 0.41 |
| Cat-2 | 0.23 |
| Cat-4 | 0.98 |
| Cat-6 | 0.97 |
| Cat-7 | 0.95 |
|  | 0.98 |

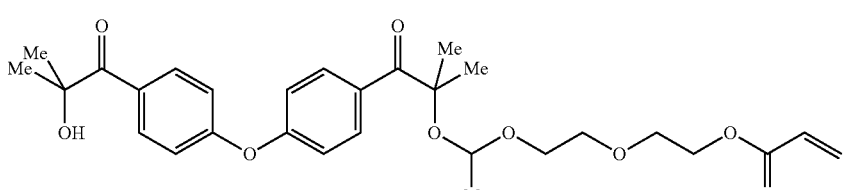

The absence of residual catalyst was double checked using TLC chromatography using methylene chloride/methanol 80/20 as eluent. The $R_f$-values are given in Table 9.

TABLE 9

| Structure | $R_f$ |
|---|---|
| Cat-2 | 0.19 |
| Cat-4 | 0.14 |
| Cat-6 | 0.33 |
| Cat-7 | 0.13 |

From this example, it becomes clear that different types of zwitterionic catalysts can be used to convert hydroxyl functionalized photoreactive compounds into asymmetric acetals according to the present invention, in the presence of high concentrations of vinyl ethers, without leaving catalyst residues in the VEEA solutions.

The invention claimed is:

1. A process for preparation of optionally asymmetric acetal compounds, the process comprising the steps of:
    reacting a compound including a hydroxyl group with a vinylether compound in the presence of a zwitterionic catalyst that includes at least one basic nitrogen containing structural fragment and at least one sulfonic acid group; wherein
    a molar ratio of the basic nitrogen to sulfonic acid is 1:1.

2. The process according to claim 1, wherein the at least one basic nitrogen containing structural fragment is selected from the group consisting of a substituted or unsubstituted pyridine group, a quinoline group, an isoquinoline group, an imidazole group, a benzimidazole group, and an aniline group.

3. The process according to claim 1, wherein the vinylether compound includes at least one vinylether group and at least one other free radical polymerizable ethylenically unsaturated group selected from the group consisting of an acrylate group, a methacrylate group, an acrylamide group, a methacrylamide group, a styrene group, a maleimide group, a vinyl ester group, a vinyl ether group, an allyl ether group, and an allyl ester group.

4. The process according to claim 3, wherein the at least one other free radical polymerizable ethylenically unsaturated group is an acrylate group.

5. The process according to claim 1, wherein the compound including a hydroxyl group is a photoreactive compound including a hydroxyl group.

6. The process according to claim 5, wherein the photoreactive compound including the hydroxyl group is a photoinitiator including a hydroxyl group or a dialkyl aniline coinitiator.

7. The process according to claim 6, wherein the photoinitiator including the hydroxyl group is selected from the group consisting of benzoinethers, benzil ketals, α,α-dialkoxyacetophenones, α-hydroxyalkylphenones, α-aminoalkylphenones, acylphosphine oxides, acylphosphine sulphides, α-haloketones, α-halosulfones, phenylglyoxalates, benzophenones, thioxanthones, 1,2-diketones, and anthraquinones.

8. The process according to claim 1, wherein a reaction scheme for the process is represented by:

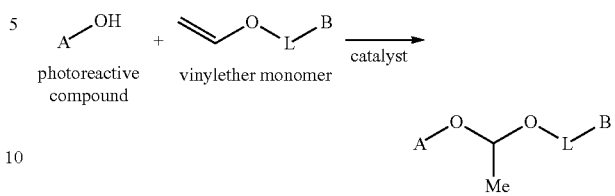

wherein

A represents a structural moiety including a photoreactive group;
L represents a divalent linking group selected from the group consisting of a substituted or unsubstituted alkylene group, alkenylene group, alkynylene group, arylene group, and a substituted or unsubstituted aliphatic ether containing group;
B represents a free radical polymerizable group selected from the group consisting of an acrylate, a methacrylate, an acrylamide, a methacryl amide, a fumarate, a maleate, and an itaconate; wherein
a starting reaction mixture of the photoreactive compound, the vinylether monomer, and the zwitterionic catalyst includes at least 25 wt % of vinylether monomer based on a total weight of the starting reaction mixture.

9. A process for preparation of optionally asymmetric acetal compounds, the process comprising the steps of:
    reacting a compound including a hydroxyl group with a vinylether compound in the presence of a zwitterionic catalyst that includes at least one basic nitrogen containing structural fragment and at least one sulfonic acid group; wherein
    a molar ratio of the basic nitrogen to sulfonic acid is 1:1;
    a reaction scheme for the process is represented by:

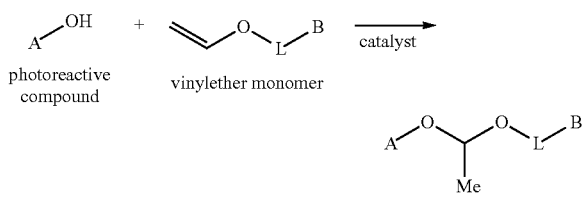

A represents a structural moiety including a photoreactive group;
L represents a divalent linking group selected from the group consisting of a substituted or unsubstituted alkylene group, alkenylene group, alkynylene group, arylene group, and a substituted or unsubstituted aliphatic ether containing group;
B represents a free radical polymerizable group selected from the group consisting of an acrylate, a methacrylate, an acrylamide, a methacryl amide, a fumarate, a maleate, and an itaconate;
a starting reaction mixture of the photoreactive compound, the vinylether monomer, and the zwitterionic catalyst includes at least 25 wt % of vinylether monomer based on a total weight of the starting reaction mixture; and
the optionally asymmetric acetal compound is represented by the Formula (INI):

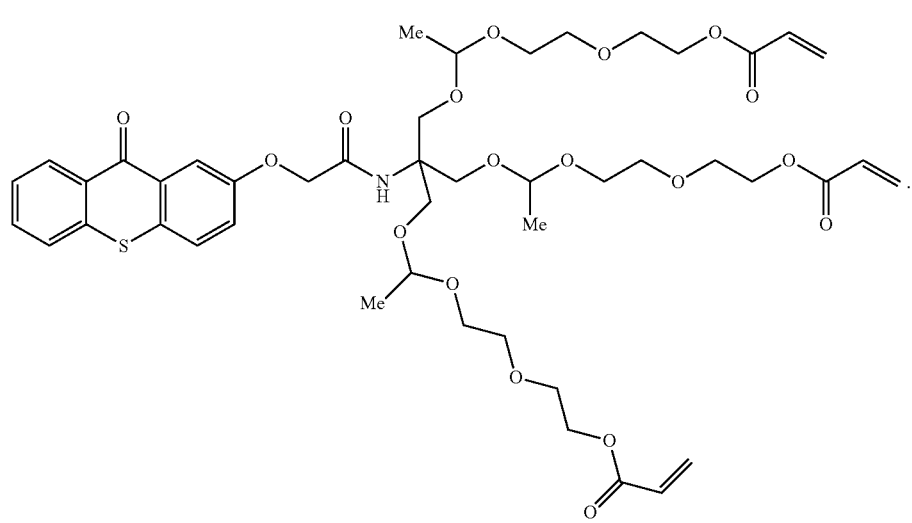

Formula (INI)

10. A polymerizable composition comprising:

a polymerizable photoreactive compound including at least one acetal;

a vinylether compound including at least one other polymerizable group;

a zwitterionic catalyst in a concentration of no more than 0.1 wt %, the zwitterionic catalyst including at least one basic nitrogen containing structural fragment and at least one sulfonic acid group in its structure, and a molar ratio of the basic nitrogen to sulfonic acid is 1:1;

optionally one or more polymerization inhibitors; and optionally one or more free radical polymerizable compounds differing from the vinylether compound including the at least one other polymerizable group; wherein the wt % is based on a total weight of the polymerizable composition.

11. The polymerizable composition according to claim 10, wherein the photoreactive compound is an acrylated photoinitiator.

12. The polymerizable composition according to claim 11, wherein the acrylated photoinitiator is selected from the group consisting of benzoinethers, benzil ketals, α,α-dialkoxyacetophenones, α-hydroxyalkylphenones, α-aminoalkylphenones, acylphosphine oxides, acylphosphine sulphides, α-haloketones, α-halosulfones, phenylglyoxalates, benzophenones, thioxanthones, 1,2-diketones, and anthraquinones.

13. The polymerizable composition according to claim 10, wherein the vinylether compound including the at least one other polymerizable group is a compound including at least one vinylether group and at least one acrylate group.

14. The polymerizable composition according to claim 10, wherein the one or more free radical polymerizable compounds differing from the vinylether compound including the at least one other polymerizable group is selected from the group consisting of monofunctional, difunctional, and polyfunctional acrylates.

15. A polymerizable composition comprising:

a polymerizable photoreactive compound including at least one acetal;

a vinylether compound including at least one other polymerizable group;

a zwitterionic catalyst in a concentration of no more than 0.1 wt %, the zwitterionic catalyst including at least one basic nitrogen containing structural fragment and at least one sulfonic acid group in its structure, and a molar ratio of the basic nitrogen to sulfonic acid is 1:1;

optionally one or more polymerization inhibitors; and optionally one or more free radical polymerizable compounds differing from the vinylether compound including the at least one other polymerizable group; wherein the wt % is based on a total weight of the polymerizable composition; and the photoreactive compound is an acrylated photoinitiator represented by the Formula (INI):

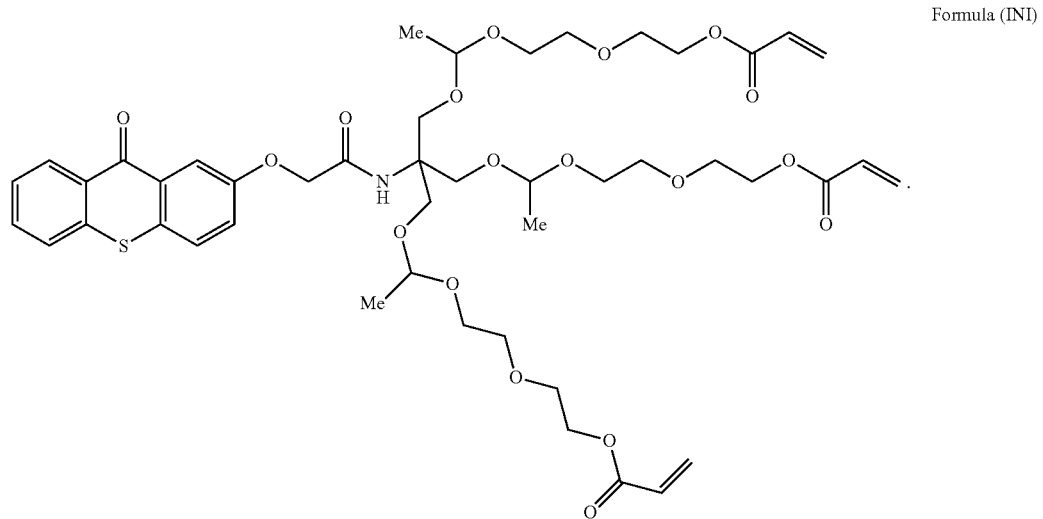 [SMILES: C=CC(=O)OCCOCCOC(C)OCC(COC(C)OCCOCCOC(=O)C=C)(COC(C)OCCOCCOC(=O)C=C)NC(=O)COc1ccc2sc3ccccc3c(=O)c2c1]
Formula (INI)